(12) United States Patent
Beutter et al.

(10) Patent No.: US 8,512,384 B2
(45) Date of Patent: Aug. 20, 2013

(54) BONE PLATE

(75) Inventors: Florian Beutter, Solothurn (CH); Werner Pauli, Huttwil (CH)

(73) Assignee: Depuy Synthes Products, LLC, Raynhamm, MA (US)

( * ) Notice: Subject to any disclaimer, the term of this patent is extended or adjusted under 35 U.S.C. 154(b) by 1975 days.

(21) Appl. No.: 11/473,903

(22) Filed: Jun. 22, 2006

(65) Prior Publication Data

US 2007/0073298 A1 Mar. 29, 2007

Related U.S. Application Data

(63) Continuation of application No. PCT/CH03/00838, filed on Dec. 22, 2003.

(51) Int. Cl.
*A61F 2/30* (2006.01)

(52) U.S. Cl.
USPC .......................................... 606/280

(58) Field of Classification Search
USPC ................ 606/69, 70, 71, 73, 280–299
See application file for complete search history.

(56) References Cited

U.S. PATENT DOCUMENTS

| | | | |
|---|---|---|---|
| 590,463 A | 9/1897 | Plopper | |
| 4,903,691 A * | 2/1990 | Heinl | 606/70 |
| 5,147,361 A | 9/1992 | Ojima et al. | |
| 5,275,601 A | 1/1994 | Gogolewski et al. | |
| 5,779,706 A * | 7/1998 | Tschakaloff | 606/281 |
| 5,868,746 A | 2/1999 | Sarver et al. | |
| 5,904,683 A | 5/1999 | Pohndorf et al. | |
| 6,206,881 B1 * | 3/2001 | Frigg et al. | 606/291 |
| 6,206,883 B1 * | 3/2001 | Tunc | 606/77 |
| 6,224,602 B1 | 5/2001 | Hayes | |
| 6,315,852 B1 | 11/2001 | Magrini et al. | |
| 6,348,052 B1 * | 2/2002 | Sammarco | 606/284 |
| 6,458,133 B1 | 10/2002 | Lin | |
| 6,602,255 B1 * | 8/2003 | Campbell et al. | 606/290 |
| 6,605,090 B1 * | 8/2003 | Trieu et al. | 606/281 |
| 6,945,973 B2 * | 9/2005 | Bray | 606/287 |
| 7,052,499 B2 * | 5/2006 | Steger et al. | 606/291 |
| 7,112,222 B2 * | 9/2006 | Fraser et al. | 623/17.11 |
| 7,137,984 B2 * | 11/2006 | Michelson | 606/279 |

(Continued)

FOREIGN PATENT DOCUMENTS

| | | |
|---|---|---|
| DE | 4038082 A | 6/1991 |
| DE | 42 01 043 | 7/1993 |
| DE | 10003968 A | 8/2001 |
| FR | 2836369 A | 8/2003 |
| JP | 47-36217 | 1/1972 |
| JP | 3-75717 | 7/1991 |

(Continued)

OTHER PUBLICATIONS

International Search Report of International Application No. PCT/CH03/00838.

*Primary Examiner* — Kevin T Truong
*Assistant Examiner* — Christopher Beccia
(74) *Attorney, Agent, or Firm* — Fay Kaplun & Marcin, LLP

(57) ABSTRACT

A bone plate having a shape of an "X". The bone plate includes an upper side, an underside facing the bone, a middle part and, adjoining thereon, a peripheral region, which encloses the four extensions of the "X" and in which four plate boreholes are accommodated. The plate boreholes have means, which are suitable for the rigid, angularly stable anchoring of bone screws which may be introduced therein.

20 Claims, 2 Drawing Sheets

(56) References Cited

U.S. PATENT DOCUMENTS

| | | | |
|---|---|---|---|
| 7,220,263 B2 * | 5/2007 | Cordaro | 606/70 |
| 7,229,442 B2 * | 6/2007 | Schafer | 606/272 |
| 7,322,984 B2 * | 1/2008 | Doubler et al. | 606/70 |
| 7,771,457 B2 | 8/2010 | Kay et al. | |
| 2006/0173459 A1 * | 8/2006 | Kay et al. | 606/69 |

FOREIGN PATENT DOCUMENTS

| | | |
|---|---|---|
| JP | 03-75717 | 7/1991 |
| JP | 7-178115 | 7/1995 |
| JP | 11-512004 | 10/1999 |
| JP | 2002-542875 | 12/2002 |
| WO | 00/53111 | 9/2000 |

\* cited by examiner

BONE PLATE

CROSS REFERENCE TO RELATED APPLICATION

This application is a continuation of International Patent Application No. PCT/CH2003/000838, filed Dec. 22, 2003, the entire contents of which is expressly incorporated herein by reference.

TECHNICAL FIELD

The present invention relates generally to bone plates.

BACKGROUND OF THE INVENTION

U.S. Pat. No. 5,868,746 to Sarver describes a generic bone plate. The Sarver patent discloses an X-shaped bone plate, which has four boreholes at its four extremities. A disadvantage of the Sarver "X"-shaped bone plate is that the four boreholes do not have any means for connecting the screws in a rigid, angularly stable manner with the plate.

German document DE-A 40 38 082 to Ojima discloses a double-T-shaped plate having four plate holes with a thread which can accommodate corresponding threaded cap screws. A disadvantage of this plate that it is not X-shaped. Thus, during bending or torsion along the plate's longitudinal axis, the plate exhibits a poor stress distribution and can therefore be stressed mainly in only one direction, namely in compression.

SUMMARY OF THE INVENTION

The present invention is to provide a remedy for the above-discussed disadvantages. It is an object of the invention to produce a bone plate, to fix bones or bone fragments stably. A further object is to achieve an optimum combination of resistance to bending and rotation, as well as to compression with a minimum of invasiveness.

The present invention accomplishes the objective set out above with a bone plate. The bone plate, having an "X" shape, may comprise an upper side, an underside, a middle part and, adjoining thereon, a peripheral region comprising four extensions of the "X", and at least four plate boreholes. At least one of the plate boreholes has means which are suitable for rigid, angularly stable anchoring of bone screws inserted into the boreholes, and the bone plate may include at least two bone screws having a head and a shaft.

Advantages achieved by the invention are essentially that an advantageous stress distribution is achieved in comparison to H-plates or double-T-shaped plates, an increased and rigid stability is made possible by the angularly stable anchoring of the screws in the plate, and the possibility exists of accommodating two screws per bone or bone fragment or osteotomy partner and of achieving rotational stability thereby.

In one embodiment, at least one of the plate boreholes has a central axis, which is not parallel to the line perpendicular to the middle part. By these means, the screws, introduced into the plate boreholes, do not collide with one another when the bone plate is pre-bent over one of the two middle axes. In particular, at least one of the plate boreholes may have a central axis which is not parallel to the line perpendicular to the middle part. Thus, one of the angularly stable screws can be set in such a manner that it goes beyond the osteotomy or the fracture, providing increased stability for the connection of the two bone fragments.

In the case of a further embodiment, the number N of plate boreholes, which have a central axis, not parallel to the line perpendicular to the middle part, is two, three or four.

In a further embodiment, at least a part of the plate boreholes may taper conically towards the underside facing the bone so that these means are suitable for realizing rigid, angularly stable anchoring of bone screws introduced into the plate boreholes. These means may also consist of an internal thread.

In the case of a further embodiment, four plate boreholes may be disposed at the corner of a rectangle. By this configuration, increased rotational stability may be realized by introducing screws bone fragment(s).

The plate boreholes may also have central axes, which are not parallel to one another. This has the advantage that screws may be used, which are introduced at an angle into the plate boreholes, in order to cross the osteotomy, the bone fracture or the joint, so that the stability also comes from the bone screw itself and not only from the bone plate in conjunction with the bone screw.

The central axes of the plate boreholes may also converge towards one another on the underside of the bone plate facing the bone. By these means, it can be avoided that the screws, introduced into the bone plate, collide with one another when the plate is bent.

The central axes of the plate boreholes may also intersect at a point. By this configuration, the bone plate can be used in any direction, without consideration to any special offset angle. The perpendicular line at the center of the middle part of the bone plate may also pass through this point.

In the case of a further embodiment, the bone plate lies in a plane. Furthermore, it may have two planes of symmetry, which are orthogonal to one another.

In another embodiment, at least two bone screws, having a head and a shaft, may be used together with the bone plate. The head of at least one of the bone screws having means, which permit a rigid, angularly stable anchoring in the plate boreholes. Preferably, the head of the at least one bone screw may be constructed conically. The head of the at least one bone screw may also consist of a material, which is harder than the bone plate in the region of the plate borehole, and the head having an external thread which, when screwed into the plate borehole, cuts a corresponding thread.

Embodiments of the screw head, cone, external thread, and harder material, represent means which permit a rigid, angularly stable anchoring in the plate boreholes.

Advantageously, the quadrangle, mounted by the four plate boreholes, has a height of 10 to 40 mm and a width of 10 to 40 mm.

At least one part of the angle, formed by the four arms of the "X", may be rounded, so that a better stress distribution results from the flattening of the stress peaks.

In the case of a further embodiment, the thickness of the bone plate may be greater in the region of the plate boreholes than in the regions between the plate boreholes. By virtue of this structure, the bone plate becomes even less invasive. On the other hand, because of the conical screw head, the minimum height in the region about the plate holes may exceed a certain value. A further advantage is that the plate boreholes are deformed only minimally if at all when the bone plate is bent.

In the case of a further embodiment, the four arms of the "X" of the bone plate can be bent with respect to the middle part, so that the bone plate can be adapted to the contour of the bone.

BRIEF DESCRIPTION OF THE DRAWINGS

The bone plate is explained in even greater detail in the following exemplary drawings. The bone plate may be better understood by reference to the following drawings, wherein like references numerals represent like elements. The drawings are merely exemplary to illustrate the structure, operation and method of use of the bone plate and certain features that may be used singularly or in combination with other features and the invention should not be limited to the embodiments shown.

DESCRIPTION OF THE PREFERRED EMBODIMENTS

Figure 1:
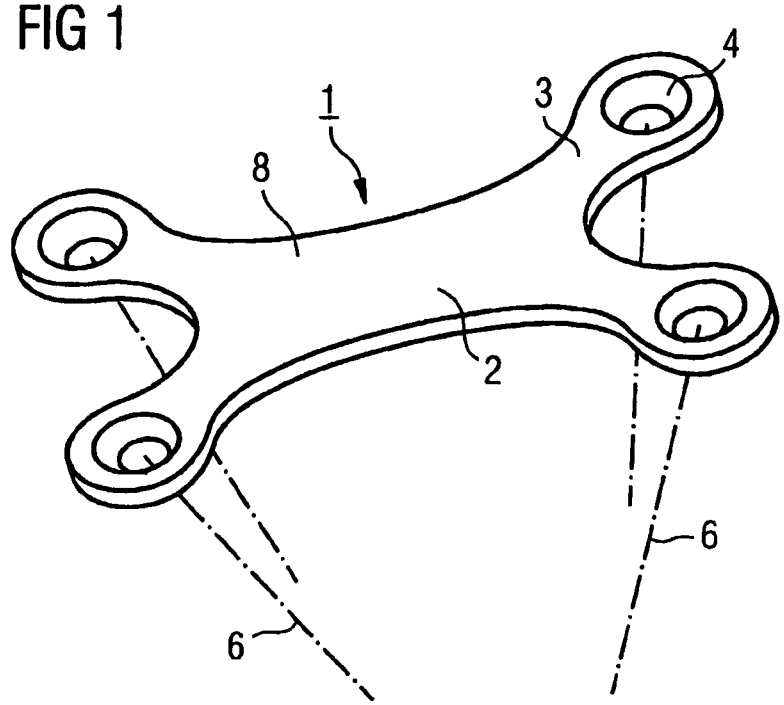
FIG. 1 shows a perspective view of an "X"-shaped bone plate with four conical plate holes.
Figure 2:
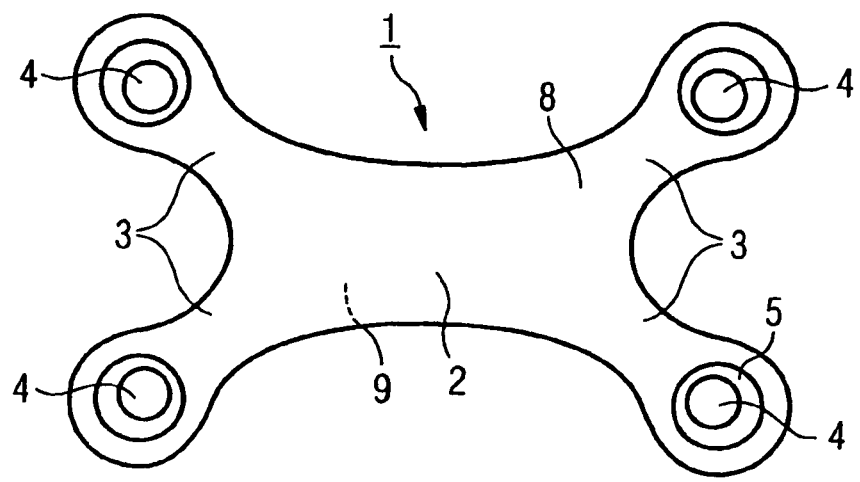
FIG. 2 shows a plane view of the bone plate of FIG. 1.

The bone plate 1, shown in FIGS. 1 and 2, may comprise an upper side 8, an underside 9 facing the bone, a middle part 2 and, adjoining thereon, a peripheral region 3, in which four plate boreholes 4 are accommodated. The four plate boreholes 4 have means 5, which are suitable for the rigid, angularly stable anchoring of bone screws 10, which are to be introduced therein. These means 5 may consist of the plate boreholes 4 tapering conically towards the underside 9. Bone screws 10 with a correspondingly conically constructed head 11 can then be connected angularly stably and in a rigid manner with the bone plate 1. The means 5, as shown in FIG. 3, may additionally comprise an internal thread 14.

The bone plate 1 may have a shape of an "X", the peripheral region 3 comprising the four arms of the "X". The four plate boreholes 4 may preferably be disposed at the ends of the four arms of the "X" at the corners of an imaginary rectangle. The angles, formed by the four arms of the "X" may be rounded.

The four plate boreholes 4 have central axes 6, which converge toward one another underneath the underside 9 of the bone plate 1 and may intersect essentially at a point 7 such that when bone screws 10 are introduced into the bone plate 1 they do not collide with one another when the bone plate 1 is bent. The normal at the center of the middle part 2 of the bone plate 1 may extend through the point 7 (FIG. 3). The bone plate 1 accordingly has two planes of symmetry, which are orthogonal to one another. By this configuration, the bone plate 1 can be used in any direction, without consideration to any special offset angle. The perpendicular line at the center of the middle part 2 of the bone plate 1 may also pass through the point 7.

Figure 3:
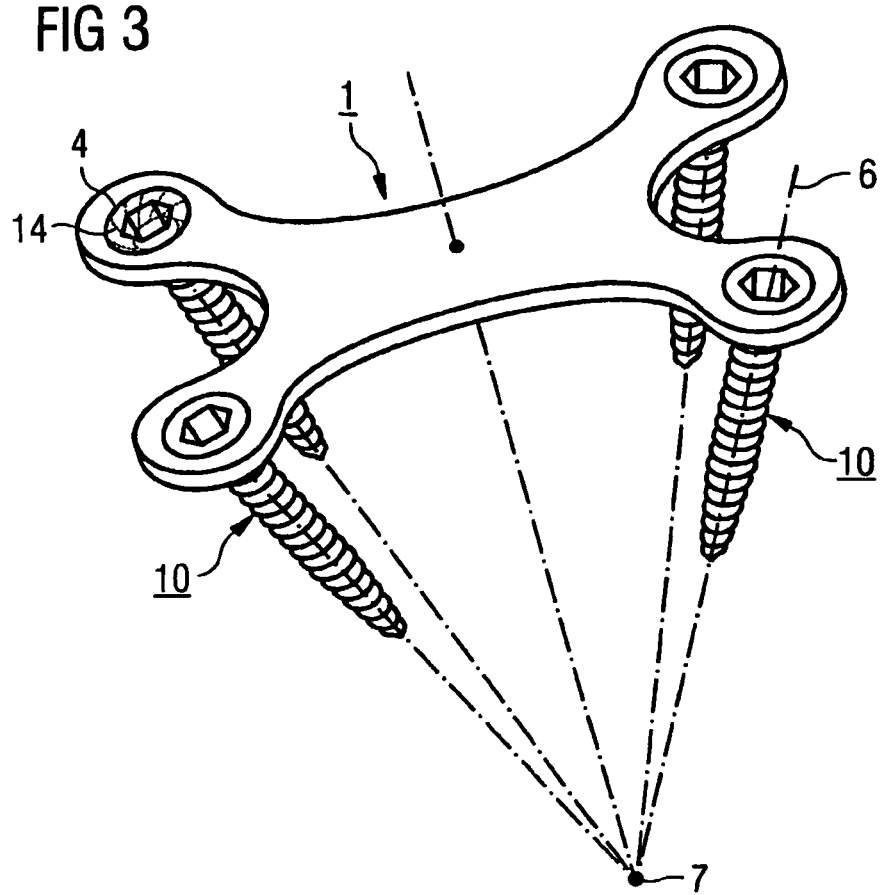
FIG. 3 shows a perspective view of a variation of the bone plate of FIG. 1 with bone screws inserted.
Figure 4:
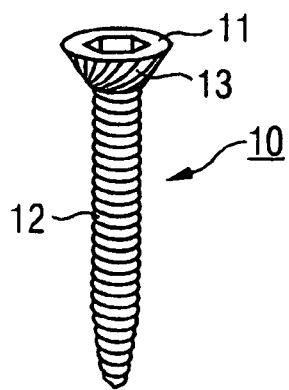
FIG. 4 shows a perspective view of a bone screw of FIG. 3.

As shown in FIG. 3, the bone plate 1 may accommodate four bone screws 10 (FIG. 4) comprising a head 11 and a shaft 12. The head 11 having means 13 in the form of a conical, external thread, which permit a rigid, angularly stable anchoring in the plate boreholes 4. The head 11 of the at least one bone screw 10 may also consist of a material, which is harder than the bone plate 1 in the region of the plate borehole 4, such that the head 11 having an external thread which, when screwed into the plate borehole 4, cuts a corresponding thread.

The bone plate 1 lies in one plane and can be bent at will by the user. The four arms of the "X" of the bone plate 1 can be bent with respect to the middle part 2, so that the bone plate 1 can be adapted to the contour of the bone. The bone plate 1 may, however, also be made available already pre-bent to the user. There may be two planes of symmetry of the bone plate 1, which are orthogonal to one another.

In one embodiment, at least one of the plate boreholes 4 has a central axis 6, which is not parallel to the line perpendicular to the middle part 2. Bone screws 10 introduced into the plate boreholes 4 do not collide with one another when the bone plate 1 is pre-bent over one of the two middle axes. One of the angularly stable screws can be set in such a manner that it goes beyond the osteotomy or the fracture, providing increased stability for the connection of the two bone fragments.

The number N of plate boreholes 4, which have a central axis 6, which are not parallel to the line perpendicular to the middle part 2 is two, three or four.

At least a part of the plate boreholes 4 may taper conically towards the underside 9 facing the bone. This tapering, means 5, may be suitable for rigid, angularly stable anchoring of bone screws 10 into the plate boreholes 4. These means 5 may also consist of an internal thread of the tapered plate boreholes 4. Bone screws 10 may be introduced at an angle into the plate boreholes 4, in order to cross the osteotomy, the bone fracture or the joint, so that the stability also comes from the bone screw 10 itself and not only from the bone plate 1 in conjunction with the bone screw.

The quadrangle, mounted by the four plate boreholes 4, may preferably have a height of about 10 to 40 mm and a width of about 10 to 40 mm. The thickness of the bone plate 1 may be greater in the region of the plate boreholes 4 than in the regions between the plate boreholes 4. Further, the minimum height in the region about the plate boreholes 4 must exceed a certain value, and that the plate boreholes 4 are deformed only minimally if at all when the bone plate is bent.

The invention claimed is:

1. A bone plate for affixing to a bone comprising:
an upper side, an underside, a middle part and, adjoining thereon, a peripheral region comprising four extensions forming a substantially "X" shape, each of the four extensions being connected to the middle part via a connecting region, the connecting region having a width that is smaller than a width of each of the four extensions, and at least four plate boreholes extending from the upper side to the underside,
wherein at least one of the plate boreholes has means which are suitable for rigid, angularly stable anchoring of bone screws inserted into the boreholes, and
wherein the bone plate is configured and adapted to receive at least two bone screws having a head and a shaft.

2. The bone plate according to claim 1, wherein at least one of the plate boreholes with means has a central axis that is not parallel to a line perpendicular to the middle part.

3. The bone plate according to claim 2 wherein a number N of the boreholes with means having a central axis are not parallel to the line perpendicular to the middle part is two, three or four.

4. The bone plate according to claim 1, wherein at least a part of the boreholes tapers conically in the direction of the underside of the bone plate.

5. The bone plate according to claim 1, wherein the means consist of an internal thread.

6. The bone plate according to claim 1, wherein the four plate boreholes are disposed at the corners of a rectangle form by the "X" shape of the extensions.

7. The bone plate according to claim 1, wherein the plate boreholes have central axes which are not parallel to one another.

8. The bone plate according to claim 7, wherein the central axes of the underside of the bone plate facing the bone converge toward one another.

9. The bone plate according to claim 8, wherein the central axes intersect essentially at a point.

10. The bone plate according to claim 1, wherein the bone plate lies in one plane.

11. The bone plate according to claim 1, wherein the bone plate has two planes of symmetry orthogonal to one another.

12. The bone plate according to claim 11, wherein the head of the at least one bone screw is conically and acts as means for rigid, angularly stable anchoring of the at least one bone screw.

13. The bone plate according to claim 11, wherein the head of the at least one bone screw has an external thread and acts as means for rigid, angularly stable anchoring of the at least one bone screw.

14. The bone plate according to claim 11, wherein the head of the at least one bone screw consists of a material harder than that of the bone plate in the region of the plate borehole and acts as means for rigid, angularly stable anchoring of the at least one bone screw.

15. The bone plate according to claim 1, wherein a quadrangle, mounted by the four plate boreholes, has a height of about 10 to 40 mm.

16. The bone plate according to claim 15, wherein the quadrangle, mounted by the four plate boreholes, has a width of about 10 to 40 mm.

17. The bone plate according to claim 1, wherein at least some of the corners formed by the four extensions of the "X" are rounded.

18. The bone plate according to claim 1, wherein a region about the boreholes is thicker than in a region between the boreholes.

19. The bone plate according to claim 1, wherein the four extensions of the "X" can be bent down with respect to the middle part.

20. A method of fixing a bone plate to a bone, the method comprising:
   selecting the bone plate having an upper side, an underside, a middle part and, adjoining thereon, a peripheral region comprising four extensions forming a substantially "X" shape, each of the four extensions being connected to the middle part via a connecting region, the connecting region having a width that is smaller than a width of each of the four extensions, and at least four plate boreholes extending from the upper side to the underside, wherein at least one of the plate boreholes has means which are suitable for rigid, angularly stable anchoring of bone screws inserted into the boreholes;
   bending the bone plate to fit the contour of the bone; and
   inserting and securing at least two bone screws having a head and a shaft into at least two of the plate boreholes,
   wherein the plate borehole means include at least a part of the boreholes tapering conically in the direction of the underside of the bone plate,
   wherein the head of at least one of the bone screws is conical in shape having an external thread and composed of a material harder than that of the bone plate in the region of the plate borehole and acts as means for rigid, angularly stable anchoring of the at least one bone screw.

* * * * *